(12) United States Patent
Majewski et al.

(10) Patent No.: US 8,017,916 B1
(45) Date of Patent: Sep. 13, 2011

(54) IMAGING SYSTEM FOR CARDIAC PLANAR IMAGING USING A DEDICATED DUAL-HEAD GAMMA CAMERA

(75) Inventors: Stanislaw Majewski, Morgantown, VA (US); Marc M. Umeno, Woodinville, WA (US)

(73) Assignee: Jefferson Science Associates, LLC, Newport News, VA (US)

( * ) Notice: Subject to any disclaimer, the term of this patent is extended or adjusted under 35 U.S.C. 154(b) by 317 days.

(21) Appl. No.: 11/824,357

(22) Filed: Jun. 29, 2007

(51) Int. Cl.
*H01L 27/146* (2006.01)
*G01T 1/20* (2006.01)

(52) U.S. Cl. ............... 250/370.09; 250/366; 250/370.11

(58) Field of Classification Search .................. 250/366, 250/370.1
See application file for complete search history.

(56) References Cited

U.S. PATENT DOCUMENTS

| | | | |
|---|---|---|---|
| RE28,451 E * | 6/1975 | Spleha et al. ................. | 250/366 |
| 4,675,526 A * | 6/1987 | Rogers et al. ............ | 250/363.02 |
| 5,444,252 A * | 8/1995 | Hug et al. ................ | 250/363.08 |
| 5,760,402 A | 6/1998 | Hug et al. | |
| 6,617,582 B2 | 9/2003 | Stark | |
| 6,671,541 B2 | 12/2003 | Bishop et al. | |
| 6,847,838 B1 | 1/2005 | Macey et al. | |
| 2002/0188197 A1 * | 12/2002 | Bishop et al. ................. | 600/436 |
| 2006/0113482 A1 * | 6/2006 | Pelizzari et al. ......... | 250/370.09 |

* cited by examiner

Primary Examiner — David Porta
Assistant Examiner — Carolyn Igyarto

(57) ABSTRACT

A cardiac imaging system employing dual gamma imaging heads co-registered with one another to provide two dynamic simultaneous views of the heart sector of a patient torso. A first gamma imaging head is positioned in a first orientation with respect to the heart sector and a second gamma imaging head is positioned in a second orientation with respect to the heart sector. An adjustment arrangement is capable of adjusting the distance between the separate imaging heads and the angle between the heads. With the angle between the imaging heads set to 180 degrees and operating in a range of 140-159 keV and at a rate of up to 500*k*Hz, the imaging heads are co-registered to produce simultaneous dynamic recording of two stereotactic views of the heart. The use of co-registered imaging heads maximizes the uniformity of detection sensitivity of blood flow in and around the heart over the whole heart volume and minimizes radiation absorption effects. A normalization/image fusion technique is implemented pixel-by-corresponding pixel to increase signal for any cardiac region viewed in two images obtained from the two opposed detector heads for the same time bin. The imaging system is capable of producing enhanced first pass studies, bloodpool studies including planar, gated and non-gated EKG studies, planar EKG perfusion studies, and planar hot spot imaging.

5 Claims, 9 Drawing Sheets

IMAGING SYSTEM FOR CARDIAC PLANAR IMAGING USING A DEDICATED DUAL-HEAD GAMMA CAMERA

The United States of America may have certain rights to this invention under Management and Operating contract No. DE-ACO5-06OR23177 from the Department of Energy.

FIELD OF THE INVENTION

1) This invention relates to cardiac imaging and more particularly to a cardiac imaging system using dual gamma imaging heads co-registered with one another to provide two dynamic simultaneous views of the heart region.

BACKGROUND OF THE INVENTION

2) Cardiac imaging and functional analysis is the largest single nuclear medical imaging application and represents the area of greatest unmet need in the current technology. Physicians require information on the anatomy and function of the heart in order to diagnose, prescribe treatment, and monitor results of intervention.

3) First-Pass Radionuclide Angiography (RNA) provides the clinician with patient information for improved patient management that is either difficult and/or costly to obtain using other technologies. First-Pass RNA procedures have substantial underutilized potential to be used as early diagnostics for coronary artery disease and myocardial infarctions. The speed and ease of administration of the First-Pass RNA diagnostic procedures allow for new use environments such as the Emergency Room environment or in outpatient cardiology clinics, First-Pass RNA can provide unique dynamic information about cardiac function, such as regional ventricular wall motion, ventricular ejection fraction, pulmonary transit-time, contractility, and shunt quantitation.

4) Currently single gamma (non-PET) nuclear medicine cardiac imaging (both tomographic SPECT procedure and planar imaging procedures) is performed with standard nuclear medicine cameras. These procedures are either performed with standard gamma cameras or with newly introduced dedicated fast rate gamma cameras (from Digirad, GVI). Both types suffer from rather poor sensitivity to detect heart abnormalities located in the further part of the heart, away from the chest wall, hence far from the closest possible approach of the camera surface. There are two contributing factors to this limited sensitivity performance related to the basic physics principles of single gamma imaging: (1) spatial resolution that decreases with distance between the heart sector and the detector head as a result of the collimator, and (2) the dominating effect of gamma ray absorption and scattering in the heart tissue and other body organs on its way towards the detector as a consequence of tissue absorption. A single compact dedicated cardiac detector allows placement of the detector directly against the chest wall and thus improves spatial resolution by minimizing the distance to heart. But this will not help with the absorption issue.

5) In the SPECT case, during the tomographic acquisition of series of images from different detector head positions around the patient torso, each sector of the heart has better visibility from some directions of closest approach to that sector (with the exception of the inner sector of the heart equally distant from all directions). In addition, computer algorithm-based modeling of the absorption and spatial resolution effects and subsequent correction of the collected data is improving the quality of reconstructed 3D data. However, the situation is diametrically different during planar imaging, and especially during the dynamic first-pass procedure, when imaging is performed from only one pre-selected imaging direction (one view) and only limited post-acquisition corrections are possible.

6) In addition to first-pass imaging, a practical and most useful imaging cardiac system should be also able to perform other imaging procedures. Some imaging procedures that will benefit from the proposed improvement in the imager include: (1) 1st pass studies, (2) planar, EKG-gated (and non-gated) bloodpool (MUGA) studies, which encompasses extensive phase analysis of the wall motion during heart cycle to appreciate potential damage to the heart muscle, (3) planar EKG-gated (and non-gated) perfusion studies, (4) planar hot spot imaging, and (5) limited positron detection via planar acquisition.

7) Planar gated (MUGA) studies are used to evaluate ventricular wall motion, and elucidate an ejection fraction based on the systolic and diastolic filling (of blood) within the ventricle. Planar perfusion studies are used to evaluate blood flow to the myocardium (left ventricle) and are quantified by established algorithms. Hot spot imaging involves detection only in areas of unique radiotracer uptake, which are higher than background. Although not widely accepted yet, positron imaging of the heart capitalizes on the ability to image metabolism and blood flow within the heart. One of the implementations of the proposed system will have the capability to perform positron imaging studies using the same detector heads but with removed collimators and operating in a coincidence mode. However, this additional function is not at the core of the present invention, which is focusing solely on improvement of single gamma imaging capability.

8) Tc-99m is the most popular label used in nuclear medicine and is in the energy range (140 keV). The major problem associated with the single-view planar (such as firstpass) cardiac imaging procedure is that the characteristic gamma radiation from Tc-99m undergoes substantial absorption when traversing tissues such as heart muscle tissue. As a result for Tc-99m, the gamma ray flux, and the associated imaging signal in the gamma camera, coming from the region of the heart away from the detector is much more attenuated than the gamma rays originating in the front part of the heart. This signal sensitivity asymmetry, can produce an effect equivalent to a less pronounced cardiovascular flow at the back side of heart, and, therefore, provides less diagnostic power as to the quality of the cardiovascular flow in that region. On a statistical basis, this asymmetry effect results in a less pronounced separation between the healthy individuals and people who have cardiovascular disease.

9) Alternative imaging labels with higher-energy gamma emissions undergoing lower absorption in the heart tissue, such as I-131 and In-113m, have been used in the past with success, but are not used in today's clinical environment, are not being manufactured in volume, and produce higher patient doses. Subject of our invention is a partial but substantial remedy to the theoretically expected and clinically observed limitation in the detection of Tc-99m gamma emission from the patient's heart which is adversely impacting the diagnostic quality of all single gamma imaging modalities but especially of the dynamic imaging of a kind performed during the firstpass procedure.

10) The dual-head cardiac imaging system proposed herein will have the following novel features to improve cardiac imaging and functional analysis:
(1) two identical compact light-weight gamma imaging detector heads, mounted on a gantry, will be precisely mechanically co-registered to each other at 180 degrees (placed opposite to each other), placed on both sides of the patient torso and fixed relative to each other, with the patient's heart encompassed by the resulting active field of view, (2) Two high precision specially designed and produced parallel hole collimators (made out of lead, tungsten, lead alloy, tungsten alloy, or mixtures of lead or tungsten powder with filling materials such as epoxy) will be precisely mechanically aligned, and the alignment will be checked using special QA procedure with line or point Co-57 radioactive sources before each patient scan, (3) Two individually produced time series of dynamic cardiac images in both detector heads will be obtained using the same start time and time clock, and will be processed as one set of time correlated images by special imaging algorithms involving multiplication of pre-processed co-registered images from both imagers for each time frame.

SUMMARY OF THE INVENTION

6) The invention is a cardiac imaging system that employs dual gamma imaging heads co-registered with one another to provide two dynamic simultaneous views of the heart sector of a patient torso. The imaging system includes a first gamma imaging head in a first orientation with respect to the heart sector and a second gamma imaging head in a second orientation with respect to the heart sector. Each gamma imaging head is in close proximity to the patient torso and in alignment with the heart sector. An adjustment arrangement is provided for adjusting the distance between the separate imaging heads and the angle of one head with respect to the other. By adjusting the angle between the imaging heads to 180 degrees and operating in a range of 140-159 keV at a rate of up to 500 kHz, the imaging heads can be co-registered. The imaging system will produce simultaneous dynamic recording of two stereotactic views of the heart thereby providing depth information to disentangle contributions from overlapping sections of the heart. The pixel values of the two co-registered images obtained in the same time bin are multiplied on a pixel-by-pixel basis, resulting in a single product image per each time bin (pixel-by-pixel) series of dynamic images obtained from the two opposed gamma imaging heads. The use of co-registered imaging heads maximizes the uniformity of detection sensitivity of blood flow in and around the heart over the whole heart volume and minimizes radiation absorption effects. A normalization/image fusion technique is implemented pixel-by-corresponding pixel to increase signal for any cardiac region viewed in two images obtained from the two opposed detector heads for the same time bin.

OBJECTS AND ADVANTAGES

7) Several advantages are achieved with the cardiac imaging system of the present invention, including:

(1) Improved diagnostic power over conventional nuclear medicine cardiac systems.
(2) A combined image having improved spatial resolution and contrast over prior art methods.
(3) A combined image that greatly improves detection of the signal from the left coronary system thereby providing an image of all three coronaries.
(4) Increased imaging sensitivity over convention imaging systems permits detection of heart abnormalities in the further part of the heart.
(5) A significant decrease in undesirable background outside the small features of interest such as coronary arteries, hot spots or plaques.
(6) An improvement in combined image normalization by using a combined flood image obtained from the flood images of the two gamma imagers and implemented by using a novel image combination algorithm.
(7) Improved 1st pass studies of the target region as a result of the high rate capability of the imaging system.
(8) Enhanced phase analysis of the wall motion during heart cycle to appreciate potential damage to the heart muscle, including planar, EKG-gated (and non-gated) bloodpool (MUGA) studies.
(9) Improved planar EKG-gated (and non-gated) perfusion studies.
(10) Enhanced planar hot spot imaging.
(11) Better positron detection via planar acquisition.
(12) Elimination of the gamma absorption effect inherent in prior art single gamma imaging systems.
(13) Elimination of the feature overlap inherent in prior art single gamma imaging systems.
(14) The ability to observe two simultaneous dynamic views of the heart region by using a system employing two sets of co-registered detector heads used in a stereotactic way.
(15) An improved method of producing two stereotactic views with one set of co-registered detector heads by timely two-step injection of the bolus with each view dynamic image associated with one injection and a specialized background-subtracting algorithm applied to the second view position.
(16) A significant reduction in the large dead zones between the individual PSPMTs in the array of photomultiplier tubes by implementation of optimized optical coupling involving a spreader window and reflective strips installed in the dead zones.

8) These and other objects and advantages of the present invention will be better understood by reading the following description along with reference to the drawings.

INDEX TO REFERENCE NUMERALS IN DRAWINGS

| | |
|---|---|
| 20 | co-registered opposed dual-head single gamma imager |
| 21 | gamma imaging head |
| 22 | gamma imaging head |
| 24 | parallel-hole collimator |
| 26 | patient torso |
| 28 | heart segment or heart sector |
| 30 | flat PSPMT |
| 32 | optical spreader window |
| 34 | scintillation array |
| 36 | window |
| 38 | reflective strip |
| 40 | heart |
| 41 | gamma imaging system, second embodiment |
| 42 | gamma imaging head |
| 44 | gamma imaging head |
| d | depth in cm of the heart sector below the surface of the heart |
| t | acquisition time in seconds |
| T | heart thickness in cm in the relevant projection plane and direction |
| μ | linear attenuation coefficient of heart tissue in cm$^{-1}$ |

DETAILED DESCRIPTION OF THE INVENTION

Figure 1:
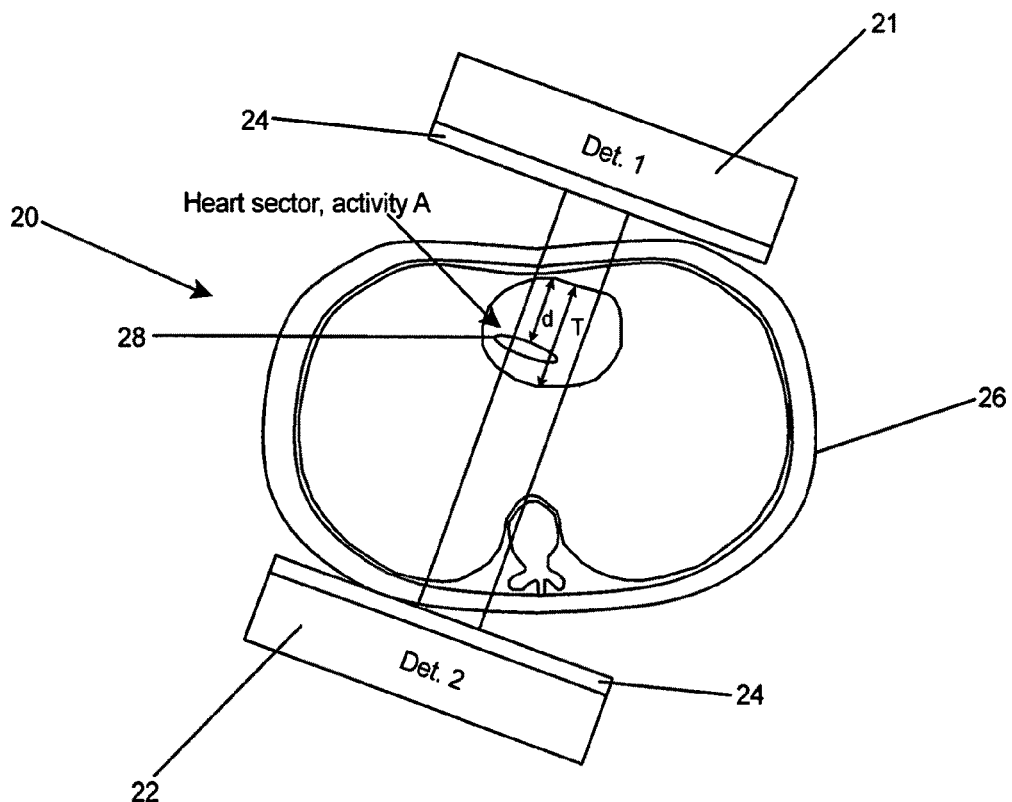
FIG. 1 is a conceptual view of a cardiac imaging system according to the present invention using dual gamma imaging heads co-registered with one another to provide two dynamic simultaneous views of the heart region.

26) The proposed invention is a system implementing two identical and opposed co-registered detector heads placed on both sides of patient's chest to provide absorption-corrected imaging for a first-pass cardiac imaging procedure. The geometry used for co-registered dual-sided imaging according to this invention is shown in FIG. 1. The co-registered dual-sided imager 20 includes two identical gamma cameras 21 and 22 with identical and co-linear parallel-hole collimators 24 placed on opposite sides of a patient torso 26. If the total radioactivity in the heart segment 28 is A, then following simultaneous acquisition of the two planar images, the number of gamma rays detected by each camera from that heart segment 28 is approximated by the following relationship:

$$N_1 = \epsilon_1 tA\exp[-\mu d] \quad N_2 = \epsilon_2 tA\exp[-\mu(T-d)] \quad (1)$$

where $\epsilon_1$ and $\epsilon_2$ are the practical detection efficiencies of cameras 1 and 2 respectively (including absorption in other than heart tissue, such as lungs, bones, etc), t is the acquisition time in seconds, μ is the linear attenuation coefficient of heart tissue in cm$^{-1}$, d is the depth in cm of the heart sector below the surface of the heart and camera 1 surface, and T is the heart thickness in the relevant projection plane and direction, in cm.

27) Each camera 20 and 22 provides a different assessment of the heart sector dynamic activity, both of which are lowered by the attenuation effect. However, if the pixel values of the two co-registered images obtained in the same time bin are multiplied on a pixel-by-pixel basis, resulting in a single product image per each time bin, then the product image gives the following for the signal value from the heart segment of interest:

$$N_1 N_2 = \epsilon_1 \epsilon_2 t^2 A^2 \exp[-\mu T] \quad (2)$$

28) Equation (2) shows that the effect of heart segment depth d is removed from the formula, with the remaining absorption effect expressed by the heart thickness T at that heart slice level, i.e., the detection sensitivity is much more uniform across the whole heart volume and higher than for any of the two individual views when used separately, or even when summed. The optimal image multiplication formula should involve more precise modeling of the heart and the surrounding varied tissues, and this will be defined during the future planned research, but even this overly simplified mathematical description shows the main feature and power of the co-registered imaging.

29) Referring to FIG. 1, geometrical parameters of the approximate formula used in the text. The heart sector with radiation activity A is at depth d below the heart surface measured in the direction of camera 20. Heart thickness at the particular cross-section level is T. The gamma rays reaching the two detectors from the selected heart sector are approximately contained within the projective tube, due to the use of parallel-hole collimators.

30) The core of the present disclosure is the use of two co-registered (pixel-by-pixel) series of dynamic images obtained from two opposed (set at 180 degree relative to each other) gamma imaging heads, to maximize uniformity of detection sensitivity of blood flow in and around the heart over the whole heart volume, with minimization of radiation absorption effects.

31) A normalization/image fusion technique is implemented pixel-by-corresponding pixel to increase signal for any cardiac region viewed in two views/images obtained from two opposed detector head positions for the same time bin. Typically 10 msec time bins will are used for fast dynamic cardiac imaging, but other time bins are possible, up to about 1 sec. The two detector head positions are geometrically aligned to better than 1 mm to achieve the required precise and unique one-to-one detector pixel correspondence.

Figure 2:
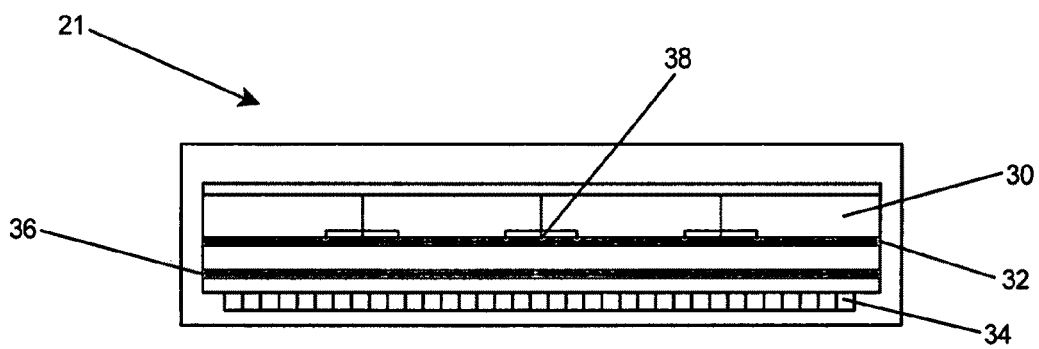
FIG. 2 is a conceptual view of gamma camera head construction based on an array of 16 flat PSPMTs.

32) An example of a camera head construction according to the present invention is shown in FIG. 2. The detector head sensor components include an array of 16 (4×4) Burle 85001-501 flat PSPMTs (Position Sensitive PhotoMultiplier Tubes) 30 coupled through optical spreader window 32 to a scintillation array 34 encapsulated behind a window 36. Reflective strips 38 are placed in the dead regions between the PSPMTs to improve scintillation light collection from the approximately 2 cm wide dead regions between the PSPMTs. The shielding and the collimator are not shown in this figure.

33) The preferred embodiment of the compact dual opposed head cardiac imager system 20 shown in FIG. 2 is based on an array of 16 Burle 85001-501 flat PSPMTs 30 arranged in a 4×4 array and coupled to a 0.6-1.2 cm thick Saint Gobain Crystals and Detectors NaI(T1) scintillator pixel array 34 having 5 mm-10 mm pixel size. This configuration is optimized for 140 keV energy photons from Tc-99m. Other PSPMT types such as Burle 85011-501, and Hamamatsu H8500 and H9500 can also be used in the gamma detector heads.

Figure 3:
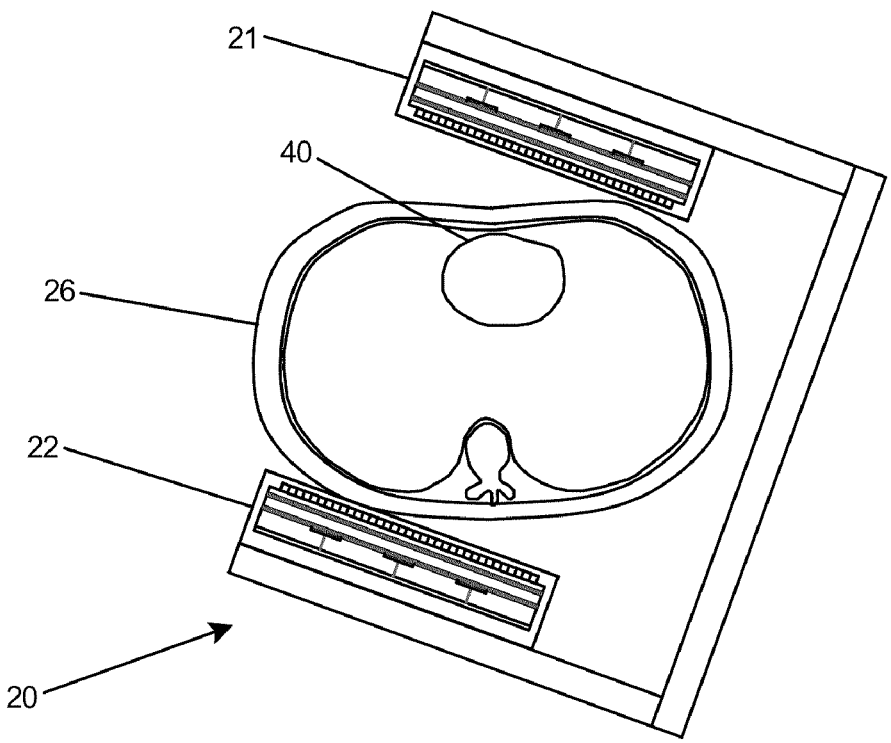
FIG. 3 is a conceptual view of a mechanically co-registered opposed dual-head single gamma imager placed at 30 deg RAO (Right Anterior Oblique) position relative to the patient's heart.

34) FIG. 3 shows an example of a dual-head imaging system 20 placed on both sides of a patient torso 26. In FIG. 3, the mechanically co-registered opposed dual-head single gamma imager 20 is placed at 30 deg RAO relative to the patient's heart 40. The second detector head 22 is placed behind the torso of a sitting or laying down patient. Detector head shielding, collimators, and patient chair or bed are not shown in this figure. The distance between the detector heads 21 and 22 can be adjusted to accommodate different situations (chair or bed) with different sized patients.

35) The support detector 22 head placed behind the back is more sensitive to the gamma rays emitted from blood flowing in the back part of the heart 40, which is much less visible to the front detector 21. The combined pixel-by-pixel image from both detectors 21 and 22 presents much more uniform sensitivity to the dynamics of blood flow throughout the heart 40, and more specifically, at the back side of the heart.

36) Each detector head images a heart by detecting emitted gamma rays. The gamma rays are emitted from a radioactive bolus such as Tc-99m, which is the most popular label used in nuclear medicine and is Man energy range (140 keV) that can be measured by the dual-headed imager system. Each imager head will operate in the gamma energy range of 140-159 keV with rate capability approaching 500 kHz. The high rate capability is the result of the design of the instrument including the capability of operating in parallel digital data flow mode for transferring digitized information from the digital imaging camera detector. This high rate performance will be especially well adapted to the so-called "first-pass" heart imaging procedure. Prior art gamma cameras in medical practice have intrinsic rate capability limited to less than about 100 kHz due in part to their slow front-end electronics and data acquisition systems.

Figure 4:
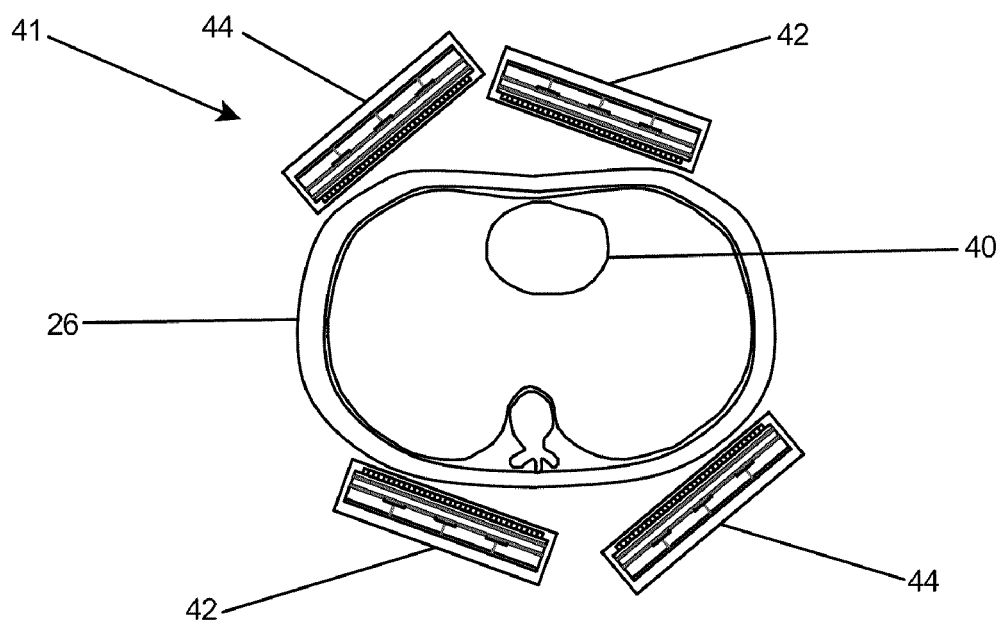
FIG. 4 is a conceptual view of a second embodiment having two pairs of compact co-registered gamma imagers providing a stereotactic view of the heart and region around the heart.

37) As shown in FIG. 4, a second embodiment of the absorption-correcting first-pass cardiac system 41 of the present invention includes two pairs of co-registered gamma detector heads 42 and 44. The use of two pairs of compact co-registered gamma imagers provides a stereotactic view of the heart and region around the heart 40. The angles and positions of the detectors 42 and 44 relative to the patient's body and the relative angles between the two pairs are flexible and adjustable within the mechanical limitations dictated by the size of the detector heads and the associated mounting gear. The simultaneous dynamic recording of two stereotactic views of the heart will provide depths information to disentangle contributions from overlapping sections of the heart. Based on these complementary views, the specialized adjunct software will de-convolve these contributions based on a dynamic model of the propagation of the injection bolus in the heart chambers and in the coronary system. This will result in the most powerful first-pass cardiac imaging system to date, free of the two key limitations of the previous single gamma imaging implementations, namely the gamma absorption effect, and the feature overlap in one view of the heart.

38) A possible third embodiment is to use the original one set of two co-registered cameras but to split the injection procedure into two injections separated by a short time of the order of about 60 seconds, with heart viewed from two different stereotactic directions. In this tightly executed timed procedure, after about 30 sec of data collection for the first view of the heart, the detector heads will be swiftly repositioned to the second view position and the new injection will be executed with a second imaging run of about 30 sec. The second injection will be adding the activity from a radioactive bolus to the activity present in the patient's body from the previous injection, but with proper modeling of the dynamic phenomena in the heart region and subsequent removal of background levels, more information about dynamics of the blood flow will be obtained than if limited to the one obtained from the first injection only. This approach enables the use of a more economical system in the highly enhanced first pass cardiac procedure. This rarely used imaging modality will be more practical to put into use as a result of the highly improved first-pass imaging procedure provided by the present invention. This allows exploitation of the full diagnostic potential for First-Pass RNA by providing crucial information about the dynamic function of the patient's heart and coronary system in a very short period of time, such as a few minutes. This powerful and unique benefit from First-Pass RNA has critical importance in emergency situations for triage and detection of potential myocardial infarctions and can be an economical, safe and reliable diagnostic for coronary artery disease, valve disease, and cardiac function used in the cardiology clinic or hospital outpatient setting.

39) The successful implementation of the proposed high performance mobile dual-head imager concept with resolution of 6-10 mm FWHM (Full Width at Half Maximum) adequate for heart imaging can provide a very useful diagnostic heart imaging tool to cardiac professionals in the ER/ICU environment.

Experimental Results:

40) The experimental system used to demonstrate the cardiac planar imager was composed of two prototype compact gamma imagers with a 20×15 cm active field of view each. Two identical high-resolution parallel-hole lead collimators were used on both camera heads. The clinical cardiac imaging situation was approximated by a torso phantom and a heart phantom. The cameras were mounted on the mammography gantry and placed at a 24 cm distance to provide space for the torso phantom.

41) An alignment procedure was performed in order to improve the resolution and significantly decrease the background radiation outside the small features of interest. To align the cameras mechanically and in software before the torso phantom studies, a special square capillary phantom is used with four capillaries filled with Tc99m activity and aligned to form a 10 cm square.

42) The four-capillary phantom was mounted on a plastic support plate in the center plane between the detectors. The capillary phantom was filled with low level activity to demonstrate also the background rejection feature of the dual-head system. The individual normalized energy spectra obtained during the capillary run are depicted in FIG. 5 and show high level of outside background (natural radioactivity, cosmic radiation, etc), in addition to the 141 keV photopeaks from Tc99m present in the capillaries.

Figure 5:
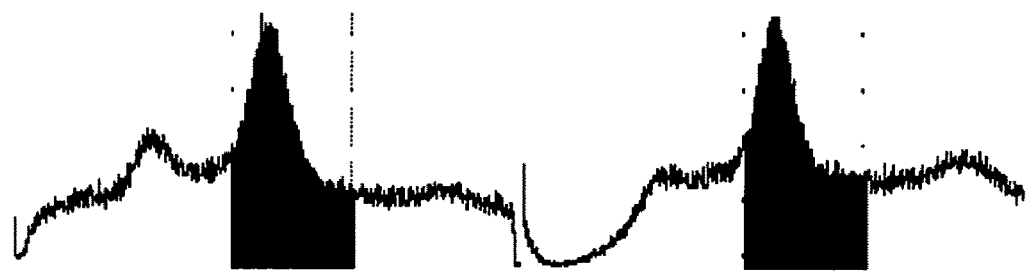
FIG. 5 depicts the normalized energy spectra (detector 1—left, and detector 2—right) obtained during a capillary alignment run of the cardiac imager system of the present invention.

43) With reference to FIG. 5, the normalized energy spectra (Detector 1—left, and Detector 2—right) obtained during the capillary alignment run show high level of background, in addition to the (shaded) 141 keV photopeak regions used in image formation for the two imagers, respectively. A rather broad energy region of 128-193 keV was used in these studies to allow for even more background in the images.

Figure 6:
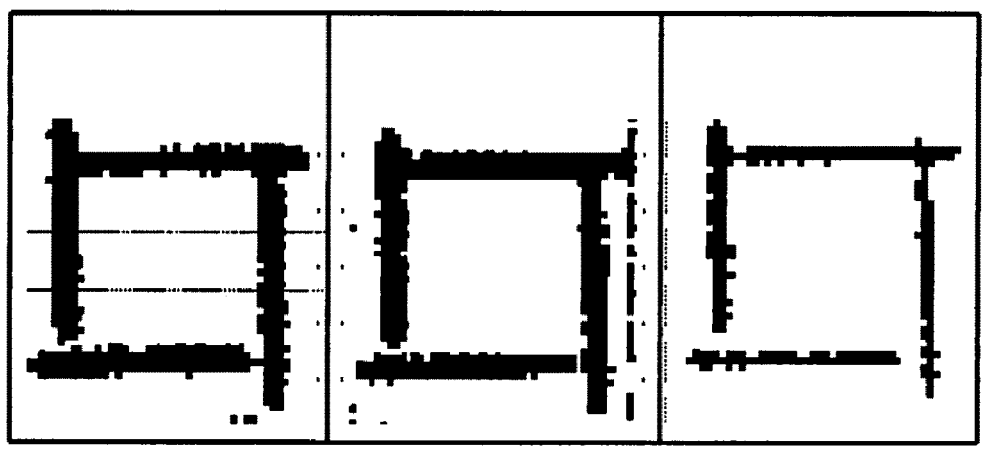
FIG. 6 depicts the phantom images from the (from left to right in the figure) detector 1, detector 2, and the combined (after mechanical and software alignment).

44) FIG. 6: The phantom images from the detector 1, detector 2, and the combined (after mechanical and software alignment) are shown in FIG. 6. Images obtained from the two detectors (left-detector 1, middle-detector 2) and the combined image at right. The horizontal lines in the left image demark a Y-strip used in all images to produce X-projective profiles, as explained below. Two features are immediately obvious from the comparison of the images above. First, the ratio of image background (present outside the capillaries) to capillary signal is lower in the combined image. Second, the capillaries are seen narrower in the combined image, which indicated higher spatial resolution than in the individual images.

Figure 7:
FIG. 7 depicts a Y-strip X-coordinate projections from detector 1 (at left), detector 2 (center), and the combined image (at right).

45) To better demonstrate quantitatively the above effects, 10-channel wide Y-strips were selected in the three of FIG. 6 and their content projected to X-coordinate. The results are shown in FIG. 7. Y-strip X-coordinate projections are shown from detector 1 (at left), detector 2 (center), and the combined image (at right). These profiles confirm substantial reduction (almost ten-fold) in background level relative to the capillary signal, and improvement in spatial FWHM resolution from about 3.5 pixels (11.2 mm) to about 2.75 pixels (8.8mm) (each image and histogram pixel is 3.2 mm wide). Benefiting from the above spatial resolution improvement using combined images, smaller heart features such as vulnerable plaques can be potentially detected, or higher resolution collimators could be implemented to increase the cardiac imaging system's dynamic sensitivity (higher image counts per each time bin).

46) For experimental phantom cardiac studies, two slightly different experimental setups were used to demonstrate the increase in detection sensitivity of the new proposed dual-imager approach to detect cardiac features such as left coronary artery placed at the back side of the heart, away from the chest wall, with the cardiac imager system configured as shown in FIG. 1.

47) FIG. 1 shows heart sector at the back region of the heart and away from detector 21 placed in the 30 deg. Right Anterior Oblique heart view position at the patient's chest wall. While the right coronary arteries are close to detector 21, left coronary arteries are away from this detector and gamma rays emitted from that far region are substantially absorbed in the heart muscle before reaching detector 21 (the absorption factor is over a factor of 2 in 6 cm of muscle tissue). It is the additional back detector 22 that is well positioned to detect the signal from the left arteries.

First Experimental Setup:

48) To simulate detection of the coronary (or other hot spot type) blood flow or uptake activity at the back side of the heart (away from the chest wall and the front detector 1) Data Spectrum Corporation's Cardiac Insert™ phantom, available from Data Spectrum Corp., Hillsborough, N.C., was used with cold torso phantom. The SPECT torso phantom is ~21.5 cm in diameter and 16.5 cm high and was filled with about 6000 cc of radioactively cold water to simulate the absorption and scatter effects of the human torso (minus the bone structures) during the first pass type procedure. A small cylindrically shaped container having a 5.5 cc volume was attached to the cardiac phantom side close to detector 2. Both the attachment and the inner approximately 100 cc ventricular volume were filled with radioactive Tc99m solution of the same activity level of about 1 μCi/cc. The outer "myocardium" 1 cm thick chamber of the cardiac phantom surrounding the inner ventricular chamber was filled with radioactively cold water. Cylindrical torso container was filled with radioactively cold water to simulate scatter and absorption in the human torso.

Figure 8:
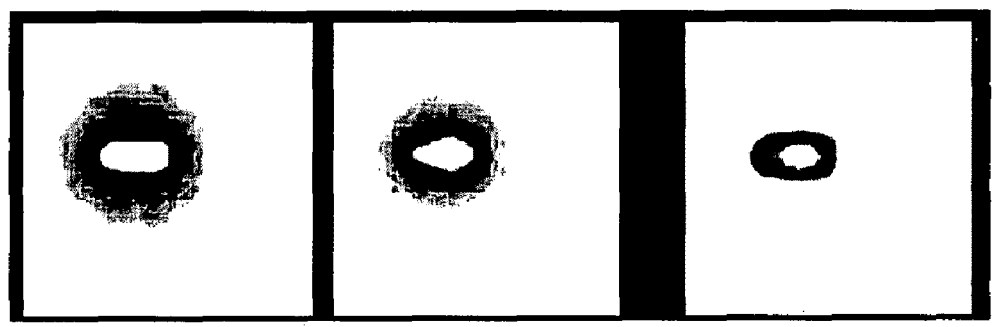
FIG. 8 depicts the processed images from the front detector 1 (image at left), back detector 2 (image in the middle), and combined (at right) for the first experimental setup.

Results from the First Setup:

49) With reference to FIG. 8, it is obvious visually that while the front detector is not seeing well the "coronary" activity behind the "ventricle" region, the back detector, close to the outside attachment, provides a strong evidence of additional activity there, while the combined image provides the strongest and cleanest signal.

Figure 9:
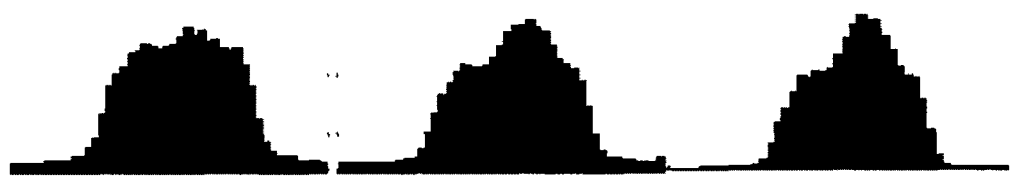
FIG. 9 shows the contrast values for the longitudinal profile plots corresponding to the three images of FIG. 8.

50) Referring to FIG. 9, the contrast values for the longitudinal profile plots in the three images depicted in FIG. 8 are ~9%, ~39%, and ~63% respectively for the front imager (left plot-detector 1), back imager (middle plot-detector 2) and overlay plot at right. (Contrast id is defined as: CONTRAST=100%*$(N_R-N_B)/N_B$), where $N_R$ is the signal value at the region of interest and $N_B$ is the signal value outside the region of interest—i.e. background.) Note that the relative background level is lowered for the combined image and structure looks "sharper" due to better spatial resolution of the combined system as compared to its two components.

Second Experimental Setup:

51) Progressing towards a more realistic situation with distributed coronary artery activity at the back of the heart, a balloon with 5.5 cc of blood-level radiation activity (the same as in the ventricle) was taped to the left side of the phantom in place of the small container as used in the previous study. A balloon filled with 5.5 cc of the blood-level activity was attached to the left side of the cardiac insert.

Figure 10:
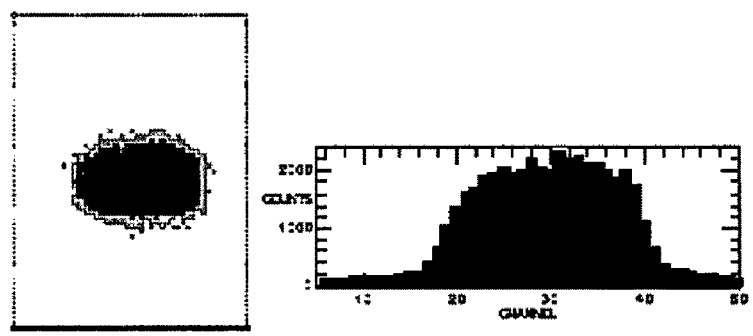
FIG. 10 depicts the raw image and longitudinal profile obtained in the first detector (detector 21 in FIG. 1) for the second experimental setup.
Figure 11:
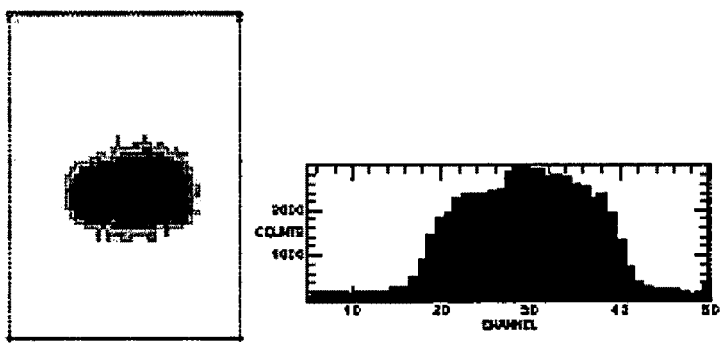
FIG. 11 depicts the raw image and longitudinal profile obtained in the second detector (detector 22 in FIG. 1) for the second experimental setup.
Figure 12:
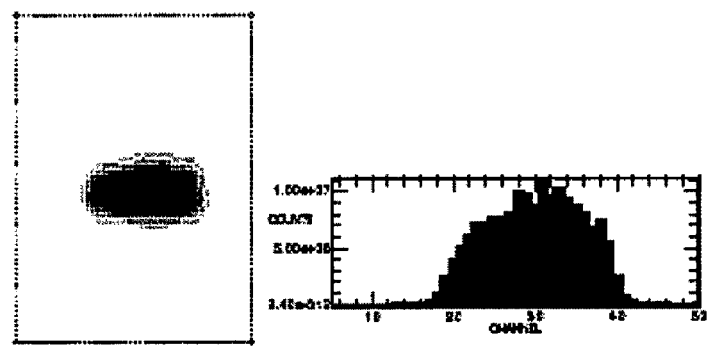
FIG. 12 depicts the combined image and longitudinal profile obtained from both detectors for the second experimental setup.

Results from the Second Setup:

52) Examples of the results obtained in the first-pass type simulation study with the attached flattened balloon at the outside wall of the cardiac insert phantom are shown in FIGS. 10-12. FIG. 10 depicts the raw image and longitudinal profile obtained in the first detector (gamma imaging head 21 in FIG. 1). There is low evidence of additional structures in the raw image of FIG. 10. FIG. 11 depicts the raw image and longitudinal profile obtained in the second detector 2 (gamma imaging head 22 in FIG. 1) Evidence of an additional signal is indicated in FIG. 11. FIG. 12 depicts the combined image and longitudinal profile obtained from both detectors. In comparison to the expected higher signal in the second detector (higher hump at the center-right), the combined additional signal is even higher, the profile slopes are sharper, and the background is highly reduced outside the image of the left ventricle.

Figure 13:
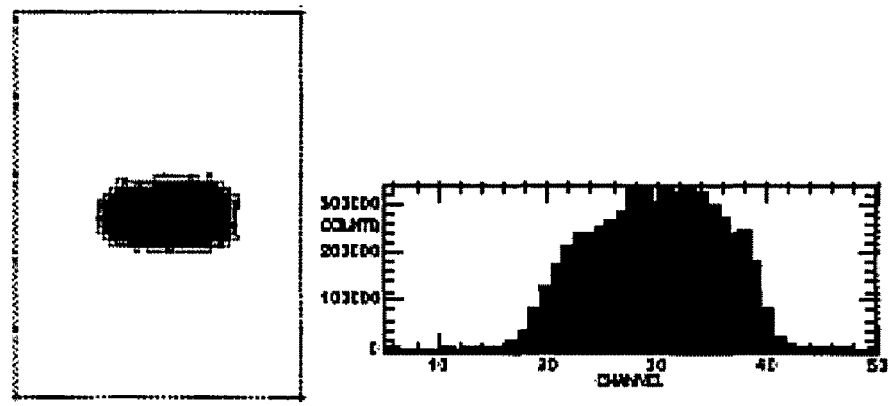
FIG. 13 is a combined image and longitudinal profile after normalization of the combined image by the combined flood image.

53) FIG. 13 depicts the combined image and longitudinal profile after normalization of the combined image by the combined flood image. The combined flood image was obtained from multiplication of the co-registered individual flood images. After normalization, the profile shows less statistical fluctuation and provides stronger evidence of the local increase in acquired signal in the region of the balloon.

Figure 14:
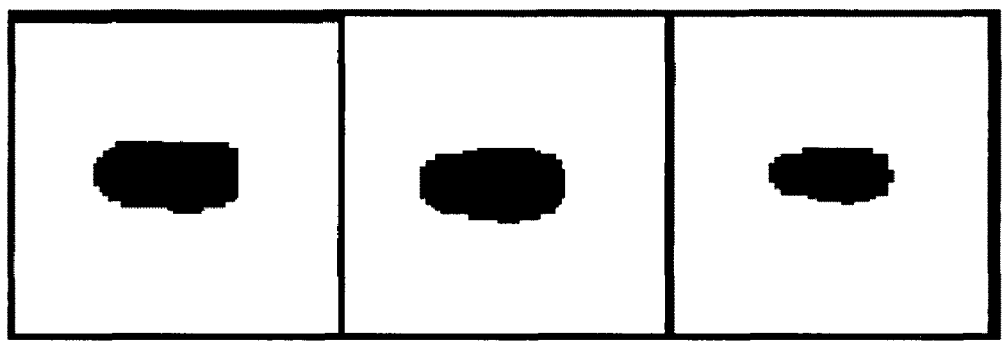
FIG. 14 depicts the three images as shown in FIGS. 10-12 but after software smoothing has been applied.

54) FIG. 14 depicts the same three images after software smoothing, with the image on the left from detector 21 (See FIG. 1), the center image from detector 22, and the right image being the combined image. The significance of FIG. 14 is that detector 1 is practically not showing the signal increase due to the balloon, while there is an indication of such an increase in detector 2.

55) In summary, the above experimental studies, performed in approximate physical conditions with substitute detectors and phantoms, provided the experimental confirmation of the theoretical concepts described herein for the present invention.

Third Experimental Setup:

56) The same experimental system was used as described in the previous experiments. The purpose of this additional study was to better simulate the realistic conditions during the first-pass cardiac imaging procedure.

57) To simulate better the realistic clinical conditions, an accurately anatomic heart cardiac phantom, available from Radiology Support Services, Long Beach, Calif., was used with a cylindrical container simulating patient's torso. The heart phantom is based on vacuum-formed shells. It was designed using high resolution CT data from a normal patient. It has the left and right ventricular chambers connected at the atrium region to make a single compartment, which can be filled and flushed independently. The volume of the heart chambers is 284 ml, while the volume of the myocardial wall is 238 ml.

58) The SPECT cylindrical torso phantom is approximately 21.5 cm in diameter and 16.5 cm high and was filled with about 6000 cc of radioactively cold water to simulate the absorption and scatter effects of the human torso (minus the bone structures) during the first pass type imaging procedure.

59) Only the left ventricle of the phantom (approximately 100 cc) was filled with Tc99m activity at a 0.3 µCi/cc level, while the rest of the phantom and the torso were filled with "cold" water. Three 2.7 mm inner diameter, 4 inches long tubes made of pieces of intravenous tube and about 0.6 cc in volume each were used to simulate the coronary arteries. They were filled each with approximately 2 µCi of activity at a ratio of approximately 10:1 to the left ventricle activity (3 µCi/cc). This choice or activities was intended to simulate the dynamic situation at the moment of the radioactive bolus being ejected with the blood flow from the left ventricular chamber to the aorta and the coronary arteries. One tube was attached outside the right ventricle region facing the right gamma camera placed at the front of the heart phantom, while two tubes were attached on the left ventricle side and close to the back detector placed behind the "patient".

60) The right detector is placed at about 30 deg. RAO (Right Anterior Oblique) position relative to the heart. The back detector is closer to the left ventricle and the two coronary arteries placed there.

61) Imaging was performed for about 25 minutes at this very low activity level. The low activity level was selected for convenience of safe working with low level activities and to satisfy low detector rate capability of this breast imaging demo system not designed for high rate operation required for cardiac imaging.

Figure 15:
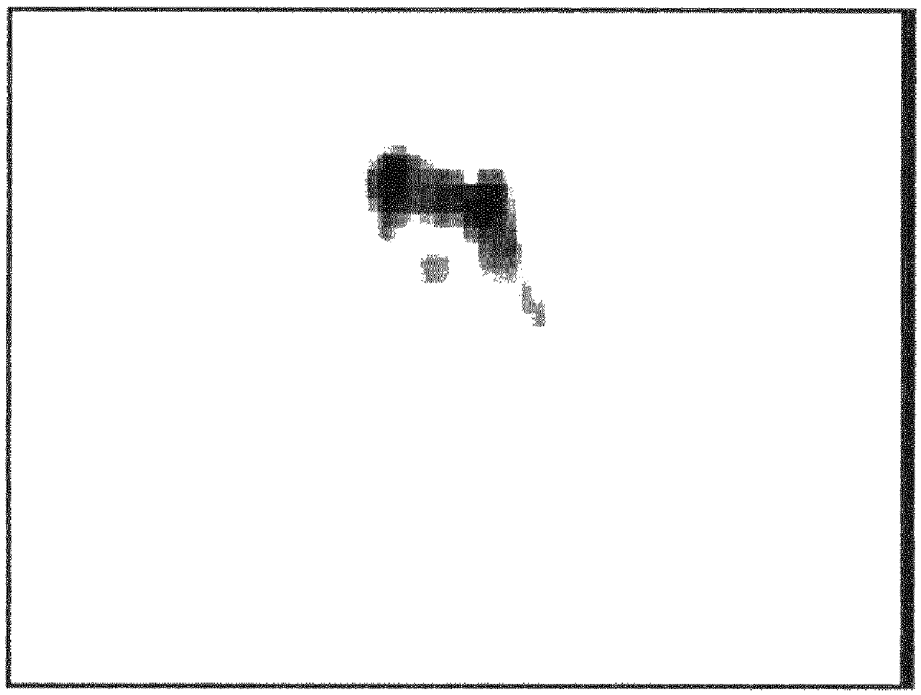
FIG. 15 depicts smoothed resulting images from the front detector for the third experimental setup.
Figure 15:
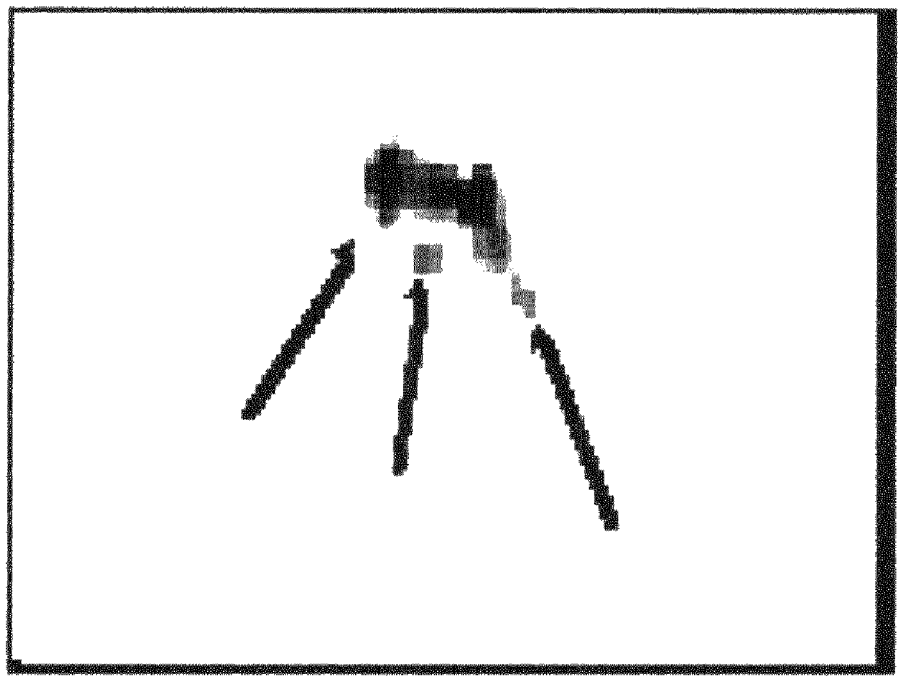
Figure 16:
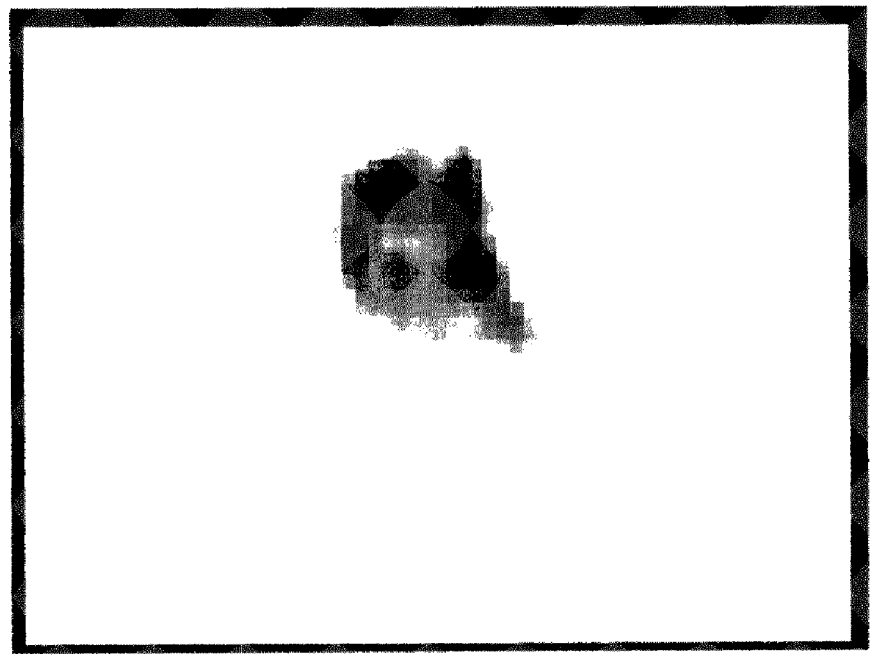
FIG. 16 depicts smoothed resulting images from the back detector for the third experimental setup.
Figure 16:
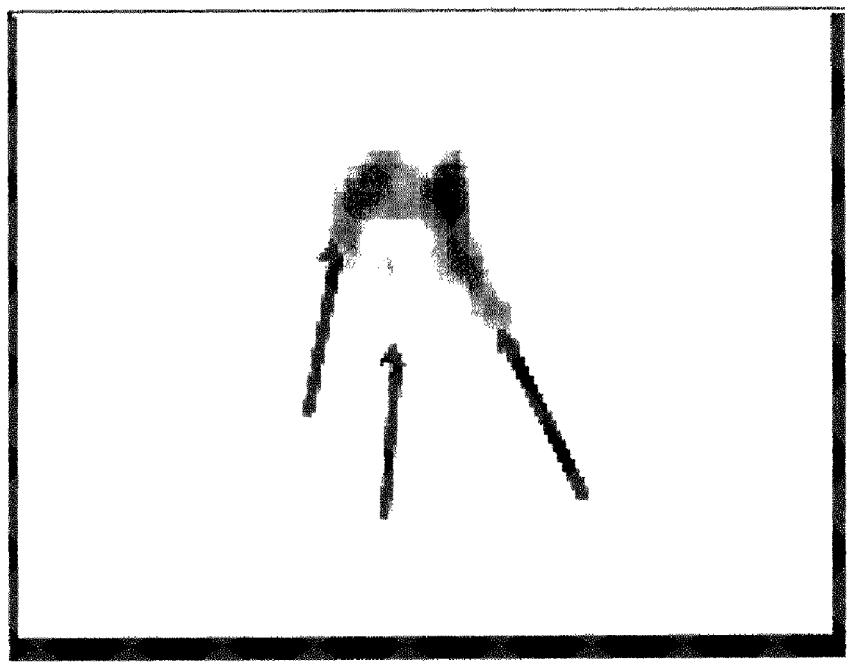
Figure 17:
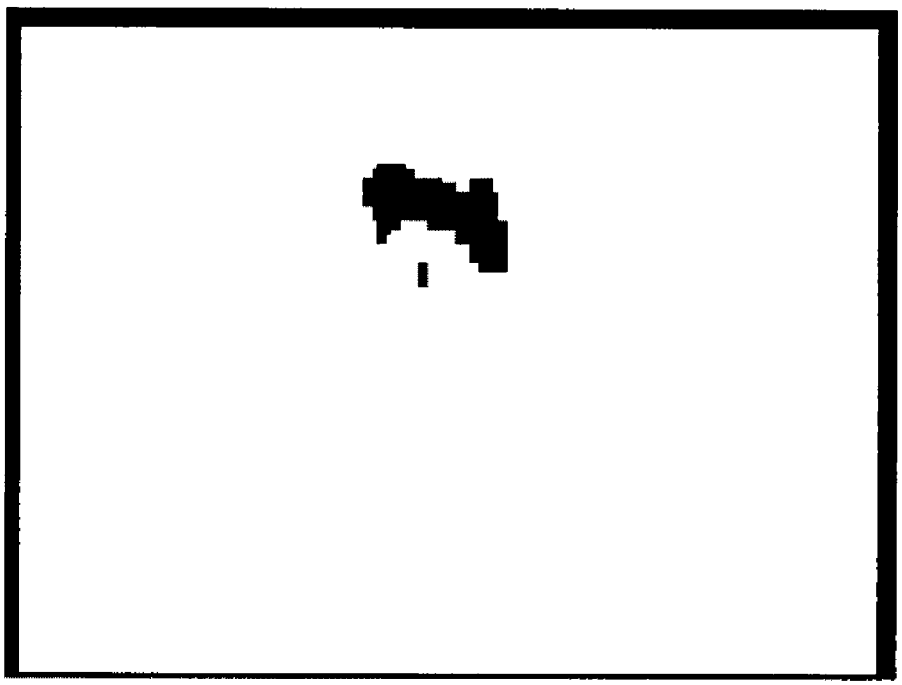
FIG. 17 depicts the combined image for the third experimental setup.
Figure 17:
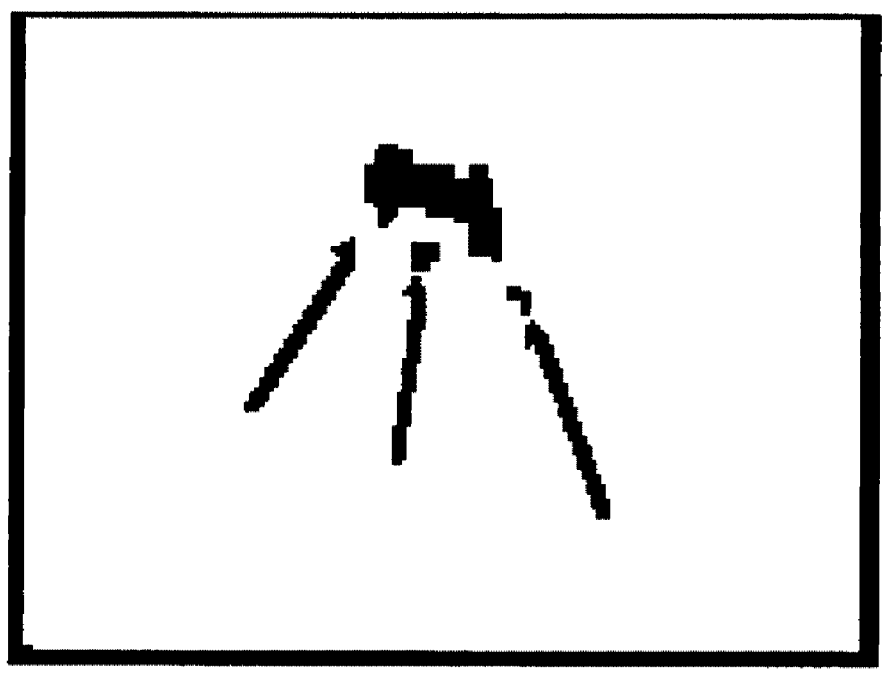

62) Smoothed resulting images, using NIH Image software, are depicted in FIGS. 15-17. The smoothed images from the front detector, as shown in FIG. 15, show some evidence of the right coronary in center (indicated by arrow) and no left coronaries visible. The smoothed images from the back detector, as shown in FIG. 16, show clear evidence of left coronaries and slight indication of the right coronary in the center. The combined image, shown in FIG. 16, shows all three coronaries as highlighted by the arrows in the figure.

63) In realistic conditions with a beating heart and coronary arteries moving with the heart muscle, detection of the signals from individual coronary arteries will be highly enhanced by using the cardiac imaging system of the present invention having dual gamma imaging heads co-registered with one another.

65) The above experimental results demonstrate again and reconfirm that addition of a second back gamma camera, co-registered with the first gamma camera, greatly improves detection of the signal from the left coronary system, therefore improving diagnostic power beyond that available from conventional nuclear medicine cardiac systems.

66) Although the description above contains many specific descriptions, materials, and dimensions, these should not be construed as limiting the scope of the invention but as merely providing illustrations of some of the presently preferred embodiments of this invention. Thus the scope of the invention should be determined by the appended claims and their legal equivalents, rather than by the examples given.

What is claimed is:

1. A single gamma imaging system for planar cardiac imaging of the heart of a patient torso treated with a radioactive bolus in an energy range of 140 keV comprising:

a first compact gamma imaging head positioned on a first side of and in close proximity to said patient torso, said first gamma imaging head in alignment with said heart and providing a first planar image;

a second compact gamma imaging head positioned on a second side of and in close proximity to said patient torso, said second gamma imaging head in alignment with said heart and providing a second planar image;

said first and second compact gamma imaging heads fixed with respect to one another and co-registered at an angle of 180 degrees relative to each other with the patient's heart encompassed by the resulting active field of view, said gamma imaging heads co-registered and operating in a range of 140-159 keV at a rate of up to 500 kHz;

parallel hole collimators including parallel holes therein on each of said gamma imaging heads;

said gamma imaging heads geometrically aligned such that each of said parallel holes in said first imaging head is aligned with a corresponding parallel hole in said second imaging head thereby creating co-linear parallel hole collimators having a one-to-one detector pixel correspondence between said imaging heads and enabling simultaneous acquisition of said first and second planar images;

for each of said first and second planar images obtained at the same time, means for normalizing and fusing each of said images pixel-by-corresponding pixel to increase signal for any cardiac region viewed in two images obtained from said two opposed detector heads for the same time bin; and said imaging system having a resolution of 6-10 mm Full Width at Half Maximum (FWHM).

2. The imaging system of claim 1 wherein said gamma imaging heads include an array of flat position sensitive photomultiplier tubes coupled to a scintillator pixel array.

3. The imaging system of claim 2 wherein said scintillator pixel array includes a thickness of between 0.6 and 1.2 cm; and a pixel size of between 5 and 10 mm.

4. The imaging system of claim 1 wherein said means for normalizing and fusing each of said images includes approximating the number of gamma rays detected by each camera from a selected heart sector by:

$$N_1 = \epsilon_1 tA \exp[-\mu d] \quad N_2 = \epsilon_2 tA \exp[-\mu(T-d)] \quad (1)$$

where N1 is the number of gamma rays detected by the first gamma imaging head, N2 is the number of gamma rays detected by the second gamma imaging head, $\epsilon_1$ and $\epsilon_2$ are the practical detection efficiencies of said first gamma imaging head and said second gamma imaging head respectively, t is the acquisition time in seconds, A is the total radioactivity in the selected heart sector, µ is the linear attenuation coefficient of heart tissue in $cm^{-1}$, d is the depth in cm of the selected heart sector below the surface of the heart measured in the direction of said first gamma imaging head, and T is the heart thickness in the relevant projection plane and direction in cm; and calculating a combined planar image by multiplying the pixel values of said first planar image and said second planar image obtained in the same time bin on a pixel-by-pixel basis according to the equation:

$$N_1 N_2 = \epsilon_1 \epsilon_2 t^2 A^2 \exp[-\mu T] \quad (2)$$

whereby said product image eliminates the effect of heart segment depth d and includes a more uniform and higher detection sensitivity than for said first planar image and said second planar image when used separately.

5. The imaging system of claim 1 wherein said first gamma imaging head is fixed at a position of 30 degree Right Anterior Oblique (RAO) relative to the heart.

* * * * *